United States Patent
Mowery

(10) Patent No.: US 10,930,395 B2
(45) Date of Patent: Feb. 23, 2021

(54) SYSTEM FOR SURGICAL DECISIONS USING DEEP LEARNING

(71) Applicant: Asheleigh Adeline Mowery, Plano, TX (US)

(72) Inventor: Asheleigh Adeline Mowery, Plano, TX (US)

(*) Notice: Subject to any disclaimer, the term of this patent is extended or adjusted under 35 U.S.C. 154(b) by 117 days.

(21) Appl. No.: 16/199,030

(22) Filed: Nov. 23, 2018

(65) Prior Publication Data

US 2020/0168334 A1    May 28, 2020

(51) Int. Cl.

| | |
|---|---|
| *G16H 50/20* | (2018.01) |
| *A61B 90/50* | (2016.01) |
| *G06N 3/04* | (2006.01) |
| *G06N 3/08* | (2006.01) |
| *A61B 34/10* | (2016.01) |
| *A61B 90/00* | (2016.01) |
| *G06K 9/00* | (2006.01) |
| *G10L 17/00* | (2013.01) |

(52) U.S. Cl.
CPC ............ *G16H 50/20* (2018.01); *A61B 34/10* (2016.02); *G06N 3/0427* (2013.01); *G06N 3/08* (2013.01); *A61B 2034/101* (2016.02); *A61B 2090/365* (2016.02); *A61B 2090/502* (2016.02); *G06K 9/00718* (2013.01); *G10L 17/00* (2013.01)

(58) Field of Classification Search
USPC ...................................... 706/11, 12; 600/182
See application file for complete search history.

(56) References Cited

U.S. PATENT DOCUMENTS

| | | | |
|---|---|---|---|
| 6,669,631 B2 | 12/2003 | Norris et al. | |
| 8,392,342 B2* | 3/2013 | Mangione-Smith | ..... A61B 6/12 706/12 |
| 9,283,675 B2* | 3/2016 | Hager | ..... B25J 9/1671 |
| 10,201,320 B2* | 2/2019 | Saget | ..... A61B 6/505 |
| 10,292,770 B2* | 5/2019 | Ryan | ..... A61B 17/7002 |
| 10,453,200 B2* | 10/2019 | Mukherjee | ..... G06T 7/143 |
| 10,582,847 B2* | 3/2020 | Raymond | ..... A61F 9/008 |
| 10,583,039 B2* | 3/2020 | Raymond | ..... A61F 2/1662 |
| 2001/0023419 A1* | 9/2001 | Lapointe | ..... G16H 50/20 706/15 |
| 2012/0109683 A1 | 5/2012 | Ebadollahi et al. | |
| 2015/0006192 A1 | 1/2015 | Sudharsan et al. | |
| 2017/0293736 A1 | 10/2017 | Kramer | |
| 2018/0012143 A1 | 1/2018 | Hansen et al. | |

(Continued)

OTHER PUBLICATIONS

"Use of a Probabilistic Neural Network to Estimate the Risk of Mortality after Cardiac Surgery", Richard K Orr, MD, MPH; Medical Decision Making vol. 17/No. 2, Apr.-Jun. (Year: 1997).*

(Continued)

*Primary Examiner* — Nina Bhat
(74) *Attorney, Agent, or Firm* — Dan B Law PLLC; Daniel S. Bretzius

(57) ABSTRACT

A method and system of training a computer learning model to improve medical care. The method and system may include training a computer learning model to obtain a predictive model that can identify success rates, potential complications, anesthesia time, and predicted life expectancy. The method and system can include inputting physiological data to generate and/or remove one or more predictive models.

15 Claims, 3 Drawing Sheets

(56) References Cited

U.S. PATENT DOCUMENTS

2018/0296281 A1\* 10/2018 Yeung .................. G06N 3/08
2018/0322254 A1\* 11/2018 Smurro ................ H04N 7/147

OTHER PUBLICATIONS

"A Bayesian Network Model for Diagnosis of Liver Disorders", Agnieszka Onisko et al., Research Report CBMI-99-27, center for Biomedical informatics, University of Pittsburgh, Sep. (Year: 1999).\*
Proposed Regulatory Framework for Modifications to Artificial Intelligence/Machine Learning Based Software as a Medical Device, Discussion Paper, USFDA publication. (Year: 2018).\*

\* cited by examiner

SYSTEM FOR SURGICAL DECISIONS USING DEEP LEARNING

CROSS REFERENCES TO RELATED PATENT

Not applicable

TECHNICAL FIELD

This invention relates to the improvement of the effectiveness of a surgeon's decision during an operation by predicting the procedural success rates and possible complications that could arise from the operation. Furthermore, a deep learning model can predict in real time the operating costs of certain procedures, prevention of medical fraud, life expectancy of patient, and, anesthesia time left until patient awakens. Finally, the next surgical steps can be predicted by a vision system using deep neural networks which can further enhance the medical care given during a complex medical operation.

BACKGROUND ART

Since the beginning of surgical history, doctors make their decisions based on their clinical and surgical experiences. Surgeons tend to provide better patient care as they age because of past experiences and by developing a basic standard of risks across every single patient based on statistical data. Although surgeons are well-respected for their level of education, surgeons don't always pick the perfect procedure to implement given a patient's condition. They also don't come across certain experiences that another surgeon may have in his or her career. Surgeons are human beings and prone to make mistakes as any normal human being would. Yet, computers do not make mistakes and can potentially acquire knowledge equivalent too and eventually beyond a surgeon's capabilities by using artificial intelligence.

If there was supporting data showing the best possible way to proceed at any point during a surgery, a surgeon would clearly pick this best path. This data could change the course of a case if the surgeon knew the risks during surgery and it could change the outcome given that the surgeon would make a certain decision or not based on the risks presented. However, surgeons don't currently have this kind of data in the operation room and it becomes more complicated as the surgery commences because the patient's condition can quickly change at any moment. Yet, if surgeons could have some technology with this knowledge that can also take into account any sudden changes in the patient given the vitals of that patient or the particular step in the surgery, then this can greatly change the course of patient care and save more lives.

There has been a rise of robotic surgeries in the past decade with robots making the surgical cut as opposed to human beings. The Da Vinci machine has been used in order to make more efficient and smaller cuts. In terms of cosmetic look, it's been a popular opinion to chose a more minimally invasive approach such as the Da Vinci to prevent larger permanent scars. It also prevents humanly mistakes such as an accidental cuts or not precise cuts from occurring. While the surgeon is still the brain behind the machine, the machine is making the physical cut. Another application just on the rise is using machine learning to help the surgeon make a surgical decision as opposed to just surgeons making their own decisions. Similar to the use of the Da Vinci machine, surgeons are using technology but they are still making the decisions. There probably won't be technology completely taking over surgeon's jobs for years to come. While machine learning takes data and can make predictive algorithms, it cannot recognize its own issues within its own algorithm without human assistance. However, with the introduction of deep learning, technology is acting more and more like the human brain continuing to learn and gather information becoming smarter and smarter over time. Deep learning is better than machine learning because it can recognize potential issues within its own system as more information is input and correct these issues without humans. It is actually a better fit in terms of healthcare since healthcare is widely founded on statistics and data. Every procedure done had to be successfully conducted thousands of times in order to be trusted and continuously be used. Surgeons and doctors use this historical data before beginning any procedure. Likewise, deep learning works in the sense that it interprets data representation and mass data to build highly accurate models.

Surgeons often use an FDA approved risk calculator to decide whether or not the surgery is worth the risk of someone's life. This calculator also includes other complications that could possibly arise during or after surgery. Millions and millions of entries are entered everyday into this calculator which ultimately builds its accuracy. However, surgeons usually do this before consulting a particular patient on their condition and before actually operating on him or her. An anesthesiologist or surgery could pull up this calculator during surgery. However, it is impractical to enter in all the patient's vital statistics into this calculator continuously during the surgery and it's more of a generalization as opposed to recognizing what can occur each step within a case. Surgeons are therefore lacking live statistics that can note the potential risks or complications that could arise given a specific time point in surgery. Moreover, the risk calculator is based on historical patient history, but does not take in account current patient changing risks as the surgery is performed. It also doesn't take into account any changes in the patients state between the time is entered into the calculator and the present time. There is an assumption that the patient stays the same which may not necessarily be true. In addition, the risk calculator is more of a historical average versus taking into account the extremes within the population which happens at both ends of the population. These extremes cause unpredicted risks in a procedure that the current risk calculator cannot usually predict.

A major issue that medicine faces would be the extremes that exist on the mass population curve, also known as the p-curve. Most people exist in the middle of the p-curve and this is where surgeries don't necessarily have "random" complications. If someone dies from the middle of the p-curve, there is usually a clear reason as to why this happened. However, the people that exist on the ends of the curve are the inexplicable cases or the certain procedures that went awry and it wasn't until the death that there was a clearer explanation. For example, there has been situations where a patient dies because of an allergy to penicillin that the patient didn't know about prior to surgery. With technological advancements, the p-curve will widen and less people will be at the ends of the curve. These "random" complications will soon not be denoted as random because of this predicative model proposed. It might be surprising to see that the extreme cases might have similarities to each other in which they can potentially be compared to each other. Eventually, the extreme can also be analyzed alongside someone in the median population who could have characteristics like someone labeled as an extreme. Therefore, there is a potential for the p-curve to widen and transfer those on the extreme end to the middle of the curve.

Some science fiction movies have introduced an interesting concept where currency is built around life expectancy. For example, someone's life is projected onto their wrists and either time can speed up or slow down depending on how time was spent. In a similar manner, imagine if someone's life can be counted down. Well human beings aren't omnipotent, but what if life expectancy can be projected when someone is in critical condition such as on an operation table. Impossible some might say to know when someone is going to die. Surgeons have spent centuries trying to estimate how much time someone has left to live based on statistics and data. Yet, they have been focusing on this data prior to or after surgery as opposed to on the table. However, the current patent described herein can predict someone's life expectancy to the last second in real time while the patient is in surgery. Furthermore, the patent described herein can provide real time risk percentages based on the surgeon's selected procedure and the possible complications that could arise given a chosen path.

This presented system will work similarly to 1980's personal computer video games such as the labyrinth 3d video game. Originally, these video games were developed to be three dimensional but actually they were programmed to be two dimensional with set three dimensional views. This invention will work similarly since there are limited amount of variable and choices to be made in a procedure especially because most procedures are done the same and are repeated. In a labyrinth, it started out where there was only two directions that the player could proceed in. However over time, more choices could be made by the player as the game was developed such as maybe going diagonally, backwards, and grabbing objects. In a similar matter, the surgical decision system can work where it starts at a simplified level and grows to include more variables and add more layers to the matrix.

Each time a surgery begins, a labyrinth is basically drawn out which represents the steps taken to get to the final end goal of having both a healthy and alive patient. Each labyrinth is drawn specifically relative to that patient, their vitals, what specific point they are in surgery given the video system and usage of object recognition, and the matching logic to other patient's similar to him or her. The labyrinth can change at any point but the system learns what is the best path to take to the end. This logic can be applied to anesthesia time, life expectancy, anesthesia medication dosages which are all variables added on to the labyrinth. This can also apply to the later suggested topic of using scans to find the best pathway to location of surgery in procedures such as the minimally invasive TAVR.

Today's operating room consist of data that is separated into different servers and devices. This makes comparing data very difficult. The operating room is connected to the cloud, but the security concerns of moving patient data is prevalent throughout our society. Moreover, there is not a direct and dynamic displaying of the patient's expense per procedure during an operation. This patent attempts to solve these issues so that a physician has a heads up display of the surgical risks, operating expenses, and schedule of events such as time left for patient to awake.

To date, there is no prior art that allows a real time predictive system that optimizes surgical decisions based on historic patient data, real time operating data, cost, prior surgical decisions, and provides an autonomous surgical prediction based on real time and historical data like previous operating procedures captured with video. The present invention learns the operating room procedures using video, sound, and surgical instrument's geotags without direct input from the operating room staff. This allows a real-time ongoing predictive model. Furthermore, the invention described herein builds a plurality of predictive models instead of just one for a faster and more accurate result. The predictive model is chosen at a certain step in the surgery and used for the most accurate prediction. Some attempted solutions have tried building encoded neural networks using Deep Learning, but none of them have a methodology to pick a different model during a medical procedure based on the current medical decision.

DISCLOSURE OF INVENTION

These and other problems are generally solved or circumvented, and technical advantages are generally achieved, by preferred embodiments of the present invention that provides for an advanced predictive method for surgery, specifically to a mechanism for predicting surgical decisions, procedural success rates, surgical complications, pharmaceutical decisions, and cost analysis using deep learning techniques.

Research has shown that the success of an operation depends on the patient's personal characteristics and the ability of the physician. The risks of a complex operation is based on the patient's heredity factors, health risks, ongoing health concerns, and unknown health issues. This patent described herein explains a method of how to lower risks and provide the best path forward during an operation. It will also shorten the length of surgeries especially when picking the next operational procedures as the surgery progresses. Instead of taking time making a firm decision, this program will help the surgeon make the best decisions based on a deep learning model.

The presently preferred embodiment of the present invention utilizes a neural network on a processing device that has been trained on the historical patient's physical data including hereditary factors, past medical history, and ongoing health concerns utilizing deep learning methods. This processing device will also be trained with surgical decisions using previous surgical videos with sound and deep learning algorithms similar to autonomous driving training with graphical processing units such that the processing device can generate a plurality of predictive models.

The second part of the presently preferred embodiment of the present invention is a method to choose a model from the previously generated plurality of predictive pre-generated models in correspondence to the current surgical decision. The method consist of a surgeon providing surgical decisions during the operation. The surgical decisions will be used to search for corresponding single predictive model from the plurality of predictive pre-generated models that references the current surgical decision.

The third part of the presently preferred embodiment of the present invention is a method to securely evaluate the current patient's vital statistics and physician's procedural decision versus the chosen trained model. This evaluation using the chosen trained model which is dynamically calculated provides a predictive cost, life expectancy, patient risk, anesthesiology timeline, and surgical procedure timeline which can be viewed securely by the physician or operating staff.

The fourth part of the presently preferred embodiment of the present invention is a detailed patient progress report which includes specific information regarding the patient's surgery including ongoing cost, procedural risks, predictive allergies or health concerns, life expectancy, anesthesiology timeline, and next suggested procedure. The fifth part of this presently preferred embodiment is the prediction of the next procedure that the surgeon will take based on ongoing operational awareness using either video, sound, mouse, keyboard or geotags on surgical tools or a combination of all these inputs. As soon as one particular path is chosen by the surgeon, the life expectancy clock will be updated and a suggested next procedure or pharmaceutical medicine to be given will be chosen by the deep learning algorithm.

Accordingly, besides the objects and advantages of an surgical decision making using deep learning described herein, and additional objective and advantage of the preferred embodiment of the present invention is to provide a secure method of interchanging data from different servers and medical devices using a secure blockchain communication method.

Another additional objective and advantage of the preferred embodiment of the present invention is to provide a secure method of interchanging data from different servers and medical devices using a secure point to point communication method, encrypted communication method, or blockchain method.

Another objective and advantage to this invention is to decrease actual surgery time because a procedural guideline with associated risks can be displayed to the surgeon as opposed to searching for a small detail about the patient that would not be immediately known.

Another objective and advantage to this invention is to predict the amount of time in each section of the surgery and the cost associated with each section. It also could predict the time it would take to complete other suggested procedures with corresponding cost to complete. This would allow the surgeon to provide the lowest risk care with the associated cost. Today surgeon's chose the best procedure for their patient, but in the case where two or more procedures were essentially equivalent, this would provide the surgeon with the lowest cost procedure with the fastest completion time.

Another objective and advantage to this patent is to assist surgeons similar to autonomous driving. Today's cars assist drivers so that there is limited intervention. This patent will allow surgeons to focus on the surgery while getting live predictive data that dynamically changes with their procedural steps in the operation. In the future, just like with autonomous driving, surgeons will use this patent with robotic assistance to completely have autonomous surgery. This will allow the surgeon to intervene only when absolutely necessary allowing the processing device to complete the surgery independent of all human assistance. Essentially, this patent is a stepping stone to autonomous surgery.

Another objective and advantage to this patent is to identify possible risks that are not known about the patient by the surgeon. These risks could be allergies, hereditary traits, hereditary risks, or other complications that came up with a patient's family members during their surgeries. Most of the time surgeries proceed as normal, but sometimes risks occur that need expedited resolution, however, vital information may not be known by the surgeon since the patient is unconscious.

Another objective and advantage to this patent is to identify the potential for a patient to awaken from under a general anesthesia. It has been shown that patients who are asleep are sometimes awake during an operation. This can be a fearful event for both the patient and anesthesiologist. However, a predictive model using patient data and operating data such as brain waves could help identify when the patient is not in a deep sleep.

Another objective and advantage to this patent is to identify when a patient is not within the normal population of previous patients. This will help the surgeon understand that there is additional risks with the current operation. This patent will help match data to drive a predictive model of relative characteristics of a patient that could drive major complications and timelines such as surgical procedures, life expectancy, time to awake, anesthesia medication dosages throughout the surgery, and operating cost.

Another objective and advantage to this patent is to use a combination of computer vision and geotags that will recognize and take into account each surgical tool or medication that is used in the surgery. This will lessen the amount of time to prepare for surgery and inventory will no longer need to be done since it will already be taken into account for. This inventory will also take part in the running cost of the surgery. This can also apply to medications and taking into account what medications are present. The geotags and computer vision can also insure that only an authorized user can use the instruments.

Another objective and advantage to patent is that wireless connectivity such as bluetooth can portably move anesthesia time on a small wireless display as the patient leaves the operation room. This will allow both the nurses and anesthesiologists to have a general knowledge as to when the patient will wake so they can plan accordingly.

Another objective and advantage to the patent is that the system will also be able to predict dosage sizes for certain medications at certain times throughout the surgery given by the matching historical data of other patient's. It will also be correlated to the other variables that has been discussed such as vital signs and the surgery vision system for further support. This will give the anesthesiologist more information in order to support their general knowledge surrounding dosage sizes. Also, the dosages will take part in the running costs. The system will know how much dosage is used based on flow control which will be taken account in cost and the amount of dosages that was originally predicted.

Another objective and advantage to the patent is that the system will not only have video cameras interpreting the surgery but also video cameras over where the anesthesiologists are. This will work in a similar manner to the other camera in which it will recognize certain medications based on packaging or label names and take this information into account in the system. It is also acts as a prevention of medical fraud where an anesthesiologist cannot accurately record what medications were used and when they were used during surgery. This will take part in the running cost calculations.

Another objective and advantage to patent is that the system is customizable for each surgeon. The surgeon is recognized either thru voice or video recognition. The system is that calibrated towards the surgeons operating room settings. Also, the system could recognize the patient in a similar fashion and have the operating room be setup for their specific characteristics such as temperature of the room. Surgeons also usually like to play music while operating so the system can upload music that the particular patient likes to work to. The system will also be able to learn not only what type of music the surgeon likes, but also the environment the surgeon likes to work best in. Also, the system will soon be able to be more customizable for different specialties. For example, the anesthesiologist can have a version or tab with information relevant to them such as predicted and anesthesia time or predicted dosages.

Cardiology will be able to have adaptations such as for TAVR where a routing system might be needed. This can also apply to neurology which is generally a very complex and tedious specialty. Therefore, it's important to be very careful in brain surgery since one slight movement in the wrong place can make major damage.

An additional embodiment of this present invention is to provide a program will include certain possible procedures to choose from given past data and success rates and failure rates. The program will rank the procedures based on relevancy and the best possible routes to proceed in. As soon as one particular path is picked, a life expectancy clock will be projected. There will be a separate tab to input the particular patient's statistics prior to surgery such as gender, age, health conditions, past surgeries, present health concerns. This will be useful also to quickly reference and act as the patient's chart. It will also be important so that past patient data can be matched up with the current patient based on similar characteristics. This will allow there to be a list the potential complications given past mass data. Vocal recognition can also be applied to this tab if the surgeon needs to know a basic statistic about the patient. Again, it will also waste less time as opposed to searching for a small detail about the patient that wouldn't be known immediately. The invention will also use its own interpretation of scans and a predicted life expectancy associated with a given a certain procedure. These scans will actually be read more thoroughly and accurate as opposed to a human brain would despite experience. In the future, a camera can be linked up to the program to receive live data images of both medical scans, such as CAT scans or an echocardiogram, and live video footage which will increase the accuracy of the both the life expectancy, procedures to give, a possibility of the patient coming out of anesthesia, and major complications that could arise. Vocal recognition will be used for easy access such as asking a question of how to proceed in a given situation or specific knowledge that needs to be known about the patient anytime throughout the case. As soon as a certain step in the procedure is chosen, the program will make its adjustments and take this into account especially in terms of the predicted life expectancy clock and other variables like anesthesia time, dosage amount, risk percentages, major complications that could arise, and surgical decisions to make given the situation.

Another objective and advantage of the additional embodiment of the patent is a projected path for surgeries that are guided with scans using the surgeries live video feed or cat scans. This can apply to certain specialties like cardiology or in neurology. In cardiology, the TAVR procedure, valve replacements are done through the femoral artery, are becoming more common but there isn't necessarily a clear path on the scan of how this is done. Therefore, this system will provide guidance with a highlighted projected path with also vocal recognition that will provide directions to the intended destination. This will be done based on the matching logic to similar patients and use similar logic to labyrinth metaphor addressed earlier. Also, the program will use object recognition in order to recognize a particular route it should proceed given that the program will be fed many scans into the system of healthy, blocked, or narrow arteries. This will allow for the combination of surgery rooms video system and live feed inside the patient for greater accuracy of the machine learning system.

Another objective and advantage of the additional embodiment of the patent is to provide complications that could arise for going the wrong path inside a patient. These complications could be shown on the display and warn the surgeon of mistakes during surgery. The system could provide new directions to a final destination similar to navigation systems in a car. The system could also provide rerouting options when a obstacle becomes apparent. This works similar to the traffic logic in the navigation system where the best route is given. However, it will be up to the doctor to proceed in a certain direction and the system will adjust accordingly. This also is a good teaching tool for younger doctors without as much experience as well. However, it can be used at any experience level of a health professional. The system will take this route into account in terms of life expectancy and any complications that could arise especially if the wrong route is taken.

Another objective and advantage of the additional embodiment of this patent is that the video interpretation system will record what is seen in the surgery in text form which will eventually eliminate the need for doctor's notes. Doctors can add additional information at the end of surgery but it won't be necessary since this system saw what everyone in the room did. This reduce the amount of workload for health professionals. Given that surgeons already spend so many hours in the operating room, this will also decrease their long work hours throughout the week. This will give the surgeons more rest time and possibly more opportunity to focus in the operating room as opposed to spending time writing these notes. Also, medical scribes in the operation room will no longer be needed. A health care technical word bank can be input into the system and the system can be taught how to write like a professional. This documentation will also be more accurate than a human being trying to recall what happened based off of memory. Furthermore, this information will take part in matching other patients to each other. The system will then become more efficient with time and experience. It will soon be able to interpret its own data input as opposed to human information put into the system. This will also prevent doctors from inaccurately reporting what happened in surgery thus preventing medical fraud. Furthermore, there will be less room for grammatical error that can lead to misinterpretation of data.

Another objective and advantage of the additional embodiment of this patent is to use DNA or hereditary searches for the patient so that a more exact model can be used. The system could use patient data or DNA data to pull up records and data to assist the accuracy of predictions.

Another objective and advantage of the additional embodiment of this patent is to use a combination of surgical data, patient data, and patient hereditary data to predict blood clots and to provide surgical decisions to overcome this obstacle.

Still further objects and advantages will become apparent from a consideration of the ensuing description and drawings. Similar constructions that do not depart from the spirit and scope of this invention set forth in the claims or embodiment should be considered the equivalent.

BRIEF DESCRIPTION OF DRAWINGS

For a more complete understanding of the present invention, and the advantages thereof, reference is now made to the following descriptions taken in conjunction with the accompanying drawing, in which.

MODE(S) FOR CARRYING OUT THE INVENTION

Detailed Description of Best Mode for Carrying Out the Invention

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to preferred embodiments in a specific context, namely an advanced predictive method of surgery, specifically to a predictive mechanism for procedural risks, operating costs of certain procedures, life expectancy, and anesthesia time left until patient awakes.

Operation of Best Mode for Carrying Out the Invention

Figure 1:
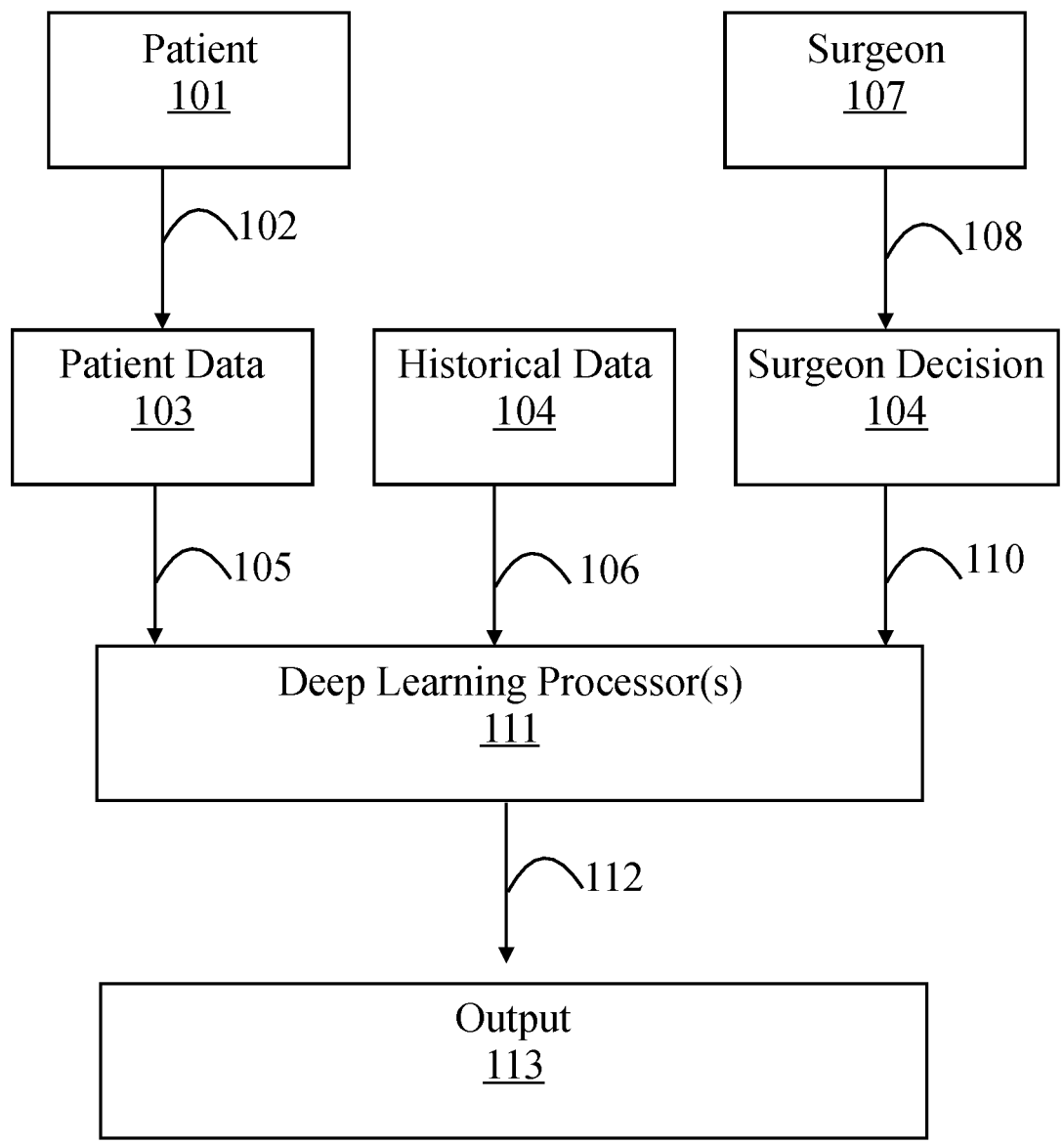
FIG. 1 is a diagrammatic illustration of a system for surgical decisions using deep learning.

Referring now to the drawings in detail, and initially to FIG. 1, a system for surgical decisions using deep learning. A patient (101) is having an operation on a specific medical issue. The patient (101) is scanned (102) for vital statistics (103) for the ongoing operation. Historical data (104) consisting of previous surgical vital statistics, hereditary data, prescription drug history, and ongoing medical issues may be found in local computer or cloud records and submitted (106) to the deep learning processor (111). The deep learning processor (111) will generate a plurality of predictive models (112) based on the submitted historical data (104). A surgeon (107) provides (108) surgical decisions (107) during the operation submitted (110) to a deep learning processor (111). The surgical decisions (107) will be used to search for corresponding single predictive model that references the current surgical decision. The next predicted surgical decisions can be preloaded in the deep learning processors to increase speed of calculation. The vital statistics (103) is used as input (105) to a deep learning processor (111) that is encoded with the single predictive model (112). The predictive model (112) provides an output corresponding to the lowest risk surgical decision, time expectancy, time for patient to wake, waiting room updates, and surgical risks displayed on an output like a display, augmented reality glasses, or mobile device.

Referring now to vital statistics (103) in detail in FIG. 1. Vital statistics could be sensors reading information like oxygen level, brain patterns, electrocardiogram, blood content, heart scans, body scans, organ scans, muscle scans, and bone scans.

Referring now to deep learning processor (111) in detail in FIG. 1. A deep learning processor utilizes a neural network to recognize patterns that works well in a systematic setting. The operating room is filled with systematic procedures in which a certain procedure is repeated over and over again. In the operating room, there are displays that project the operations on the screens to assist everyone in the room with having a better view of the operation. It becomes more difficult to see when more and more people surround the patient. Therefore, there is video cameras that basically show what the surgeon is seeing. There will also be other video camera interpreting and recognizing the medications that the anesthesiologists are using. From this footage, the program could live footage as to how the operation is preceding. It'll be able to interpret this in a similar manner as to how autonomous cars read signs on the street. This is known as computer vision basically through the use of neural networks to interpret data. Billions of different versions of the same image are input into a program and then the computer is able to interpret what it is. Videos are basically a sequence of images but together so this program will be able to interpret these images in the chronological order it is put into the system. In this manner, the program will be able to further predict the next step in the surgery. As the program becomes more and more intelligent, it'll be able to interpret this footage and apply it to its statistics and calculations. As of now, the program will use past data and data input before the surgery to assist the surgeon. However, in time the program can evolve to taking both past and live data into account. In a similar way to a child learning, the program will soon learn to become as knowledgeable or even more knowledgeable as a surgeon. As more surgeries are input, the smarter the program will become and apply this knowledge to past historical data from patient files. If the videos taken in surgery are somehow saved and specified under each patient, it'll make the program's predictions more accurate. Eventually this program will be able to predict possible complications from live data before it happens with indications or warnings of something possibly going wrong before even the surgeon notices. This can also be applied in terms of anesthesia where there can be warnings as to the patient possibly coming out of anesthesia.

Referring now to historical data (104) in detail from FIG. 1. Historical data can be related to other patient's surgery information that is available for processing. This invention could also use technology in order to read input scans which contains files of the patients as well as the scans. Epic software is an example of a form of data storage for all the patient information in a hospital, local regional area, or nationally connected medical centers. This software is password protected for only use of a healthcare professional as well as only being used in a hospital setting. Epic software's setup varies with each specialty as well as at different hospitals. A way to possibly gain information to be used in the deep learning model is through removal of the patient's names because that would follow HIPPAA protocol. The program will only be used in a hospital setting and not taken out of that setting for any other use. Therefore, professionals will be using this information and they already have an agreement to keep personal information confidential for each patient. Eventually, the goal is to have all the statistics in every operating room in the United States and maybe even one day around the world. As stated elsewhere, the more information the program has, the more accurate the diagnosis will be. Even though human beings are all different, they are very much the same in many ways.

Referring now to surgical decisions (107) in detail from FIG. 1. Surgical decisions may be entered through a mouse, keyboard, video interpretation or audio commands. Surgeons often dictate the certain steps they are going to do while operating to direct everyone in sort of a team fashion. It is sort of a follow the leader dynamic. In which, the leader is the surgeon and he or she is dictating how to go about the particular surgery. Their hands are preoccupied with doing the surgery. So, the best way to use the program would be through vocal recognition similar to that used with the common voice recognition software on mobile phones or standalone voice devices. This program will act as another tool to help the surgeon without interrupting his flow of work. It will also be used as a form of multitasking with the priority still being the patient.

Referring now to deep learning processor (111) and plurality of predictive models (112). The making and using of a deep learning processor or deep learning model is essential to this patent. However, one skilled in the art of deep learning can develop this model using advanced GPU processors. It should be appreciated, however, that the present invention provides many applicable deep learning concepts that can be embodied in a wide variety of specific contexts. The specific embodiments discussed are merely illustrative of specific ways to make and use the invention, and do not limit the scope of the invention.

Referring now to an output (113) in detail in FIG. 1. After a certain procedure is chosen, a life expectancy clock will be provided to the operating room. The patient's predicted life expectancy will be displayed based on the branching logic and ultimately the deep learning analysis. The life expectancy clock can change as the deep learning algorithm takes into account new data. The output (113) could be displayed on a graphical interface or augmented reality glasses that only certain hospital employees can view during an operation. Also, the output (113) could be a mobile application device running on a mobile device. Another output of this device could be waiting time and important health information to family members waiting in the waiting room. Family members could see this information and be informed of predicted time to completion of the surgery. Moreover, the mobile application could also show the predicted and actual cost of the ongoing surgery.

Another embodiment of the output (113) could display the predicted time life for a patient to awake which would be provided to the anesthesiologist. According to Current Procedural Terminology (CPT) guidelines, anesthesia begins when the anesthesiologist prepares the patient and then end as soon as the anesthesiologist is said to leave the room, which is also when the surgery is over. Intubation is placing breathing tubes through vocal cords to help a patient breath especially during a surgery. Intubation time is measured from when a tube is placed down a patient's trachea to assist with ventilation to when it is removed. However, extubation refers to taking the breathing tubes outside of a patient. Anesthesiologists make sure a patient can breathe on their own and usually determine this by seeing if a person is awake or following commands. This extubation time would vary depending on the complexity of a case. For example, it would occur in the intensive care unit for a cardiovascular case as opposed to in the operation room causing a lengthier extubation time. Intubation time as well as extubation time are documented in patient records. Specifically, extubation time is noted for ICU cases such as those for cardiovascular surgery. Extubation is usually done when a patient is awake and following commands. This would indicate that a person is able to breathe on his or her own. Length of a case usually can correlate to how long a person is awake or following commands. However, this is not always the case. It usually refers to when a patent is in the operation room. Intubation time, extubation time, and length of a case are documented in patients' records. All of which are variables that help predict when general anesthesia wears off and the patient wakes up. There is a general time frame as to when a patient should wake up but there is yet a way to determine an exact time until he or she wakes up.

Anesthesiologists are trained to know the dosage sizes based on the medical literature and they formed their reasoning on dosages based in experiments in which mass data of the effect of the particular dosages were recorded. Similar to the risk calculators, anesthesiologists are using statistics to make their decisions. There is also a pump which gives a recommended dosage of each drug to the patient. The anesthesiologist acts and is the final decider on whether the prediction is accurate. As opposed to the life expectancy clock, which will record a patient's predicted life expectancy in minutes. An anesthesia clock could predict a time in which a patient will awake based on various variables and a deep learning model. Some of theses variables can include length of a case, intubation time, extubation time, medication dosages, family medical history, historical records of other patients, and an individual's statistics all of which are documented. This clock will give the anesthesiologist extra reassurance that their dosage calculations are correct. However, the clock may not be able to account for everything like genetics could play a part. This is a lacking knowledge that anesthesiologists are trying to figure out the influences of dosages on some certain type of genetics. Since past data will be recorded in minutes and protocol for billing is all based on minutes, the clock will project out a time. Anesthesiologists use either online calculators or hand calculations of dosages to give the particular patient prior to surgery. The anesthesia time is recorded in patient records as a main form of billing, but it can also be used to take for a more efficient time accuracy. Alongside the calculations made by the anesthesiologist, this program will have past data of anesthesia times of other patients. As described earlier, the program will match the particular patient to another patient and from that, display the time. Ultimately, the anesthesia time will be more accurate as opposed to just having the calculation from the anesthesiologist. This will provide more efficiency and a less probability of a patient coming out of anesthesia in the middle of a surgery. This will also lessen the risk of the patient dying as well as the probability for a lawsuit especially since anesthesiologists are said to be sued frequently. However, this is just a prediction and nothing is for sure. It just gives a more accurate time duration given past data.

Description of Additional Mode for Carrying Out Invention

The making and using of the additional preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to an additional embodiments in a specific context, namely surgical decisions using deep learning to predict life expectancy, surgical decisions, and risks as shown in FIG. 1 using branch prediction or probability tree. A probability tree could be used in conjunction with the deep learning algorithm so as to filter out unrelated patient or historical data. The system will use a probability tree to search through the input patient records and match the current patient to its best match. Similar to the logic of looking for an organ door or blood donor, the program will look for the closest match. Therefore, the more patient records input into the program, the more accurate the match will be. There are billions of people in the world and although everyone is different, they are very much the same in many ways. It is also similar to the logic of a dating website. A dating website usually works in which a person inserts their basic information such as their hobbies, interests, or occupation. In the same way, patient's stats will be entered. The program will use branching logic to match the patient to a match. It'll first start at a characteristic such as gender, then branch off to age, branch off to past medical history including hereditary and DNA, then branch off to smaller details until it finds the closest match based on past records. Eventually, it will reach a branching point where it'll try to match a certain procedure to the original procedure input into the program. Eventually, the program can evolve to take into account a quick change of procedure to apply to the deep learning portion of the invention. After the branching logic commences, the program will get to a point where procedures will be chosen. Based on the pick, a clock will start running after it-takes into a count the branching logic. This is where a majority of deep learning commences. Deep learning is a form of data representation in time analysis of deep learning. From this logic, the life expectancy clock and the anesthesia clock will run.

Operation of an Alternate Mode for Carrying Out the Invention

Figure 2:
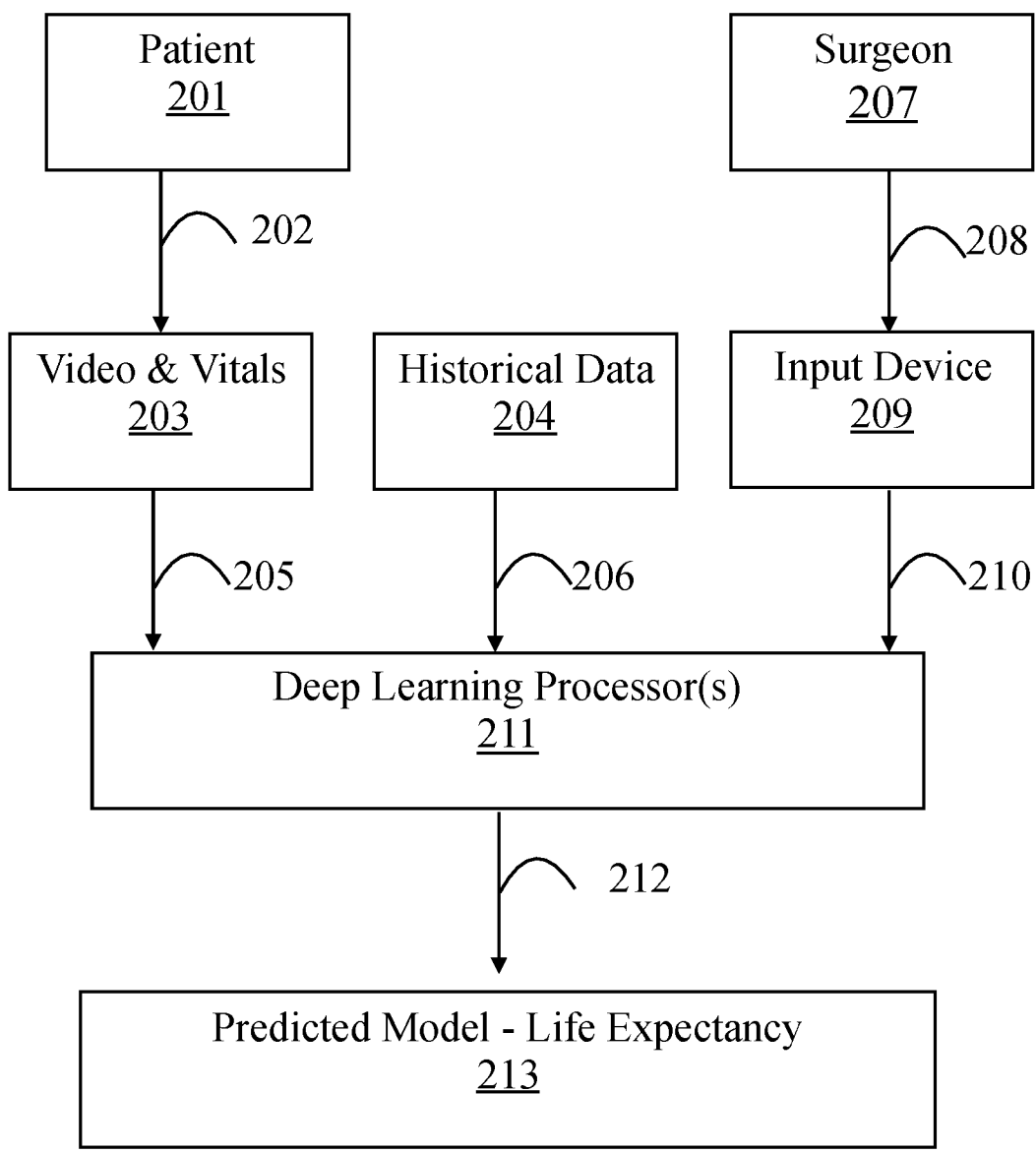
FIG. 2 is a diagrammatic illustration of a semi autonomous surgical system with limited surgeon intervention that is used in combination with a deep learning algorithm.

Referring now to the drawings in detail, and specifically to FIG. 2, which is a semi-autonomous surgical system with limited surgeon intervention that is used in combination with a deep learning algorithm. A patient (201) is having an operation on a specific medical issue. The patient (201) is viewed (202) by an operation video camera (203) and scanned (202) for vital statistics (203) for the ongoing operation. Historical data (204) consisting of previous surgical vital statistics, hereditary data, prescription drug history, and ongoing medical issues may be found in computer or cloud records and submitted (206) to the deep learning processor(s) (211). The deep learning processor(s) (211) will generate a plurality of predictive models (212) based on the historical data (204). Moreover, a surgeon (207) completing the operation inputs (208) his surgical decisions using an input device (209). The input device (209) could be keyboard, mouse, voice, or actual video of the operation. The input device (209) also is feed into the neural network (211). The surgical decisions (208) will be used to search for corresponding single predictive model that references the current surgical decision. The next surgical decisions can be preloaded in the deep learning processors to increase speed of calculation. The video and vital statistics (203) is used as input (206) to a deep learning processor(s) (211) that is encoded with the single predictive model (213). The predictive model (213) provides an output corresponding to the lowest risk surgical decision, time expectancy, time for patient to wake, waiting room updates, and surgical risks displayed on an output like a display or mobile device.

Referring now to neural network (211) and predictive model (212). The making and using of a neural network or deep learning model is essential to this patent. However, one skilled in the art of neural network or deep learning can develop this model with the assistance of advanced GPU processors. It should be appreciated, however, that the present invention provides many applicable deep learning methods that can be embodied in a wide variety of specific contexts. The specific embodiments discussed are merely illustrative of specific ways to make and use the invention, and do not limit the scope of the invention.

Figure 3:
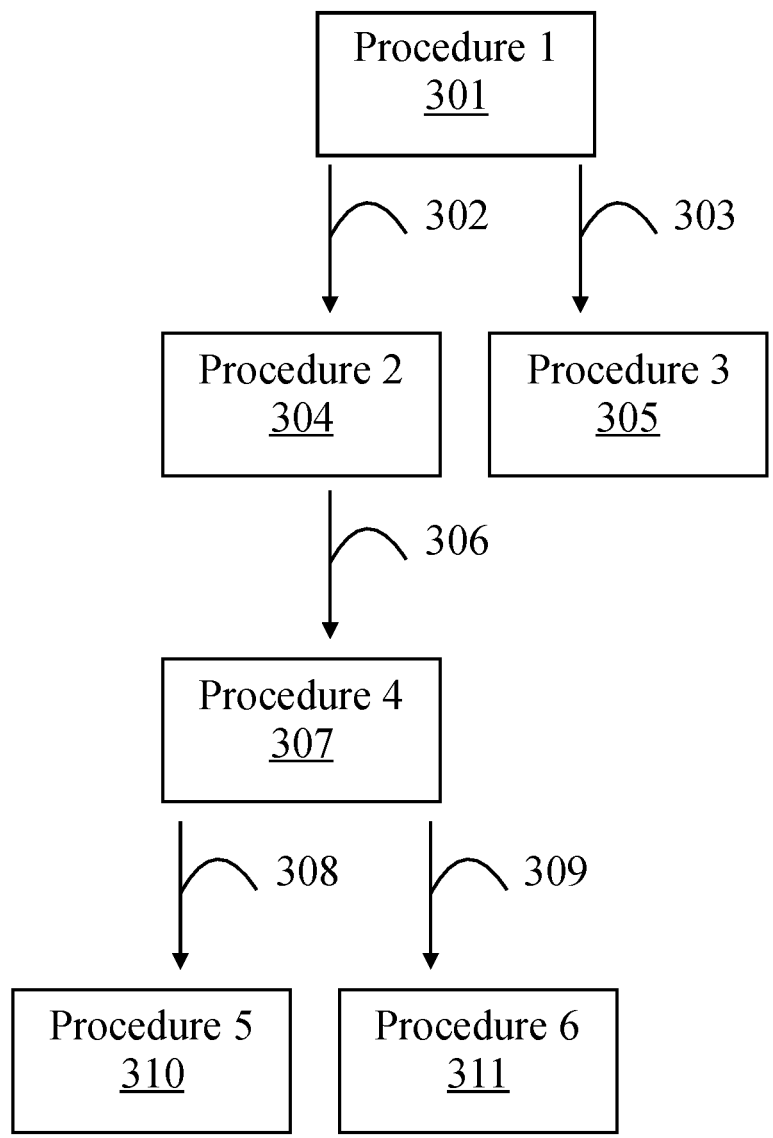
FIG. 3 is a diagrammatic illustration of the lowest risk surgical path which depends on a predictive deep learning model.

Referring now to FIG. 3, which relates to the methodology of deciding which encoded model is loaded into the neural network, the initial procedure 1 encoded model (301) is loaded into the neural network. A patient begins the operation and the patient's vital statistics and operation inputs are passed into the procedure 1 encoded model (301). Procedure 2 encoded model (304) is predicted (302) by procedure 1 encoded model (301). Also, procedure 3 encoded model (305) is predicted (303) by procedure 1 encoded model (301). Both procedure 2 encoded model (304) and procedure 3 encoded model (305) can be preloaded into a neural network for the next surgical decision. Based on the doctor's direction though video or input device, procedure 2 encoded model (304) or procedure 3 encoded model (305) will be chosen. If procedure 3 encoded model (305) is chosen, it is the last procedure in the patient's operation. Based on the number of procedures in an operation, a prediction on length of time can be generated. If procedure 2 encoded model (304) is chosen, the patient's vital statistics and operation inputs are then passed into the new model. Procedure 4 encoded model (307) is predicted (306) by procedure 2 encoded model (304). It is the only procedure model predicted. The patient's vital statistics and operation inputs are then passed into the new chosen procedure 4 encoded model (307). Procedure 5 encoded model (308) is predicted (310) by procedure 4 encoded model (301). Also, procedure 6 encoded model (311) is predicted (309) by procedure 4 encoded model (301). Both procedure 5 encoded model (308) and procedure 6 encoded model (311) can be preloaded into a neural network for the next surgical decision. Based on the doctor's direction though video or input device, procedure 5 encoded model (308) or procedure 6 encoded model (311) will be chosen. If procedure 5 encoded model (308) or procedure 6 encode model (311) are chosen, it is the last procedure in the patient's operation.

INDUSTRIAL APPLICABILITY

Accordingly, the industrial applicability of this patent is for a sellable biomedical device allowing for reliable surgical decision using deep learning, specifically to an autonomous surgical prediction using video and audio deep learning of the next surgical decision.

SEQUENCE LISTING

Not applicable

I claim:
1. A method of training a learning model to predict a surgical complication, the method comprising:
    inputting into the learning model a patient's historic information, the patient's historic information selected from the group consisting of hereditary factors, past medical history, previous medication usage, previous surgical history, gender, and age;
    inputting into the learning model an inventory of historic surgical decisions, the inventory of surgical decisions selected based on previous surgery data;
    generating, by the learning model, a plurality of predictive models based on the patient's historic information and historic surgical decisions input into the learning model;
    removing one or more of the plurality of predictive models to obtain a subset of the plurality of predictive models;
    providing a predicted complication based on the subset of the plurality of predictive models; and generating a predictive clock based on the subset of the plurality of predictive models and the predicted complication.

2. The method of claim 1, wherein the learning model comprises a deep learning model.

3. The method of claim 1, further comprising:
repeating one or more of the steps of the method until a smaller subset of the plurality of predictive models is obtained.

4. The method of claim 1, further comprising:
inputting into the learning model a patient's current data, the patient's current data selected from the group consisting of intubation time, extubation time, current active medication, and current physiological data;
wherein generating the plurality of predictive models, by the learning model, is also based on the input of the patient's current data.

5. The method of claim 4,
wherein the patient's current data comprises current physiological data,
wherein inputting the patient's current physiological data comprises:
inputting the patient's current physiological data at a first point in time; and
inputting the patient's current physiological data at a second point in time, and
wherein generating the plurality of predictive models, by the learning model, is also based on both the patient's current physiological data at the first point in time and the patient's current physiological data at the second point in time.

6. The method of claim 5, wherein the patient's current data comprises current physiological data selected from the group consisting of pulse, oxygen level, brain wave patterns, electrocardiogram data, blood test results, and organ scans.

7. The method of claim 5, further comprising:
predicting the patient's physiological data at a third point in time, and
wherein generating the plurality of predictive models, by the learning model, is also based on the predicted patient's physiological data at a third point in time.

8. The method of claim 7, wherein the predictive clock is a life expectancy clock.

9. The method of claim 1, further comprising:
inputting into the learning model a patient's current data, the patient's current data selected from the group consisting of intubation time, extubation time, current active medication, and current physiological data;
wherein removing one or more of the plurality of predictive models further comprises removing the one or more predictive models based on the input of the patient's current data.

10. The method of claim 9,
wherein the patient's current data comprises current physiological data,
wherein inputting the patient's current physiological data into the learning model comprises:
inputting the patient's current physiological data at a first point in time; and
inputting the patient's current physiological data at a second point in time, and
wherein removing one or more of the plurality of predictive models further comprises removing the one or more predictive models based on both the patient's current physiological data at the first point in time and the patient's current physiological data at the second point in time.

11. The method of claim 10, wherein the patient's current data comprises current physiological data selected from the group consisting of pulse, oxygen level, brain patterns, electrocardiogram data, blood test results, and organ scans.

12. The method of claim 1, further comprising:
inputting into the learning model an identity of a current surgical action,
wherein generating the plurality of predictive models, by the learning model, further comprises generating the plurality of predictive models based on the identity of the current surgical action, and
wherein removing one or more of the plurality of predictive models further comprises removing the one or more predictive models based on the identity of the current surgical action.

13. The method of claim 12, further comprising obtaining the identity of the current surgical action, and wherein obtaining the identity of the current surgical action comprises using live audio-visual data for a current surgery.

14. The method of claim 1, further comprising:
inputting into the learning model an amount of anesthesia effect remaining, and
generating, by the learning model, the plurality of predictive models based on the amount of anesthesia effect remaining, and
wherein the predictive clock is an anesthesia clock.

15. The method of claim 14, further comprising:
monitoring a patient's brain wave signal; and
determining the amount of anesthesia effect remaining based on the monitored brain wave signal.

* * * * *